(12) United States Patent
O'Sullivan et al.

(10) Patent No.: US 9,119,609 B2
(45) Date of Patent: Sep. 1, 2015

(54) ROTATING CELL COLLECTION DEVICE

(71) Applicant: Cook Medical Technologies LLC, Bloomington, IN (US)

(72) Inventors: Donagh O'Sullivan, Ballina-Killaloe (IE); Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 157 days.

(21) Appl. No.: 13/800,295

(22) Filed: Mar. 13, 2013

(65) Prior Publication Data

US 2014/0276210 A1 Sep. 18, 2014

(51) Int. Cl.
*A61B 10/02* (2006.01)
*A61B 10/00* (2006.01)

(52) U.S. Cl.
CPC .......... *A61B 10/02* (2013.01); *A61B 2010/0074* (2013.01); *A61B 2010/0216* (2013.01)

(58) Field of Classification Search
CPC ........... A61B 10/02; A61B 2010/0216; A61B 2010/0255; A61B 2010/0291; A61B 2010/0074
USPC .................................. 600/562, 569, 570, 572
See application file for complete search history.

(56) References Cited

U.S. PATENT DOCUMENTS

| | | | |
|---|---|---|---|
| 3,308,825 A * | 3/1967 | Cruse ............................ | 604/267 |
| 3,996,938 A | 12/1976 | Clark, III | |
| 4,465,072 A | 8/1984 | Taheri | |
| D300,060 S | 2/1989 | Molgaard-Nielsen | |
| 4,927,412 A | 5/1990 | Menasche | |
| 4,958,621 A | 9/1990 | Topel et al. | |
| 4,989,614 A | 2/1991 | Dejter, Jr. et al. | |
| 5,037,379 A | 8/1991 | Clayman et al. | |
| 5,048,538 A | 9/1991 | Terwilliger et al. | |
| 5,060,658 A | 10/1991 | Dejter, Jr. et al. | |
| 5,083,572 A | 1/1992 | Pokorny | |
| 5,137,030 A * | 8/1992 | Darougar ....................... | 600/570 |
| 5,146,921 A | 9/1992 | Terwilliger et al. | |
| 5,249,583 A | 10/1993 | Mallaby | |
| 5,253,652 A | 10/1993 | Fast | |
| 5,287,587 A | 2/1994 | Mann | |
| 5,423,745 A | 6/1995 | Todd et al. | |
| D360,260 S | 7/1995 | Brandt | |
| 5,476,104 A * | 12/1995 | Sheahon ........................ | 600/570 |
| 5,488,958 A | 2/1996 | Topel et al. | |
| D369,857 S | 5/1996 | Booth et al. | |
| 5,535,756 A | 7/1996 | Parasher | |
| 5,702,413 A | 12/1997 | Lafontaine | |
| 5,713,369 A | 2/1998 | Tao et al. | |
| 5,749,883 A | 5/1998 | Halpern | |
| 5,797,953 A | 8/1998 | Tekulve | |
| 5,976,170 A * | 11/1999 | Levin ............................. | 606/197 |

(Continued)

*Primary Examiner* — Max Hindenburg
(74) *Attorney, Agent, or Firm* — Brinks Gilson & Lione

(57) ABSTRACT

A medical device for collecting cells includes a rotatable drive wire having a proximal portion, a distal portion, an offset portion of the distal portion, and a head member attached to the offset portion. The drive wire is coupled to an axially translatable rack member via a rotation mechanism that converts axial translation of the rack member into rotation of the drive wire. The offset portion of the drive will rotate eccentrically relative to the longitudinal axis of the drive wire to increase the diameter of the rotation of the head portion. The head portion can contact an inner surface of the body cavity to collect cells, and the eccentric rotation of the head member can limit trauma experienced by the patient relative to traditional scraping of a cell collection brush.

24 Claims, 7 Drawing Sheets

(56) References Cited

U.S. PATENT DOCUMENTS

| | | |
|---|---|---|
| 6,346,086 B1 | 2/2002 | Maksem et al. |
| 6,468,228 B1 | 10/2002 | Topel et al. |
| 6,685,718 B1 | 2/2004 | Wyzgala et al. |
| 6,800,083 B2 | 10/2004 | Hiblar et al. |
| 6,843,792 B2 * | 1/2005 | Nishtala et al. ............ 606/113 |
| 7,252,674 B2 | 8/2007 | Wyzgala et al. |
| 7,641,620 B2 | 1/2010 | Wingler |
| 7,878,983 B2 | 2/2011 | Karpiel |
| 8,034,022 B2 | 10/2011 | Boatman |
| 8,057,496 B2 | 11/2011 | Fischer, Jr. |
| 8,070,691 B2 | 12/2011 | Desilets et al. |
| 8,100,881 B2 | 1/2012 | Hoffa |
| 8,123,769 B2 | 2/2012 | Osborne |
| 8,246,641 B2 | 8/2012 | Osborne et al. |
| 8,251,917 B2 * | 8/2012 | Almazan ............ 600/566 |
| 8,282,661 B2 * | 10/2012 | Eckman ............ 606/160 |

* cited by examiner

ROTATING CELL COLLECTION DEVICE

BACKGROUND

The present invention relates to cell collection devices. More particularly, the invention relates to a cell collection device having an eccentric rotating head for collecting cells.

Cell collecting devices, or cytology devices, are well known in the art. A traditional cell collection device can be in the form of a cytology brush. A cytology brush can generally be used by being inserted into a body cavity of a patient, where the brush can contact the body cavity wall to collect cells. Cytology brushes are generally elongate, and include a distal end having a plurality of bristles extending radially outward. The brush can be in the form of a metallic coiled wire, and the bristles can be disposed between the coils. The coiled nature of the brush allows it to generally bend and navigate various tortuous body vessels. Additionally, the coils allow the brush to retain its pushability for delivering the brush through the anatomy.

However, the brushes can be ineffective in collecting a sufficient number of cells and can lead to irritation or bleeding during the cell collection process. The distal end of the brush is generally narrow and has a limited surface area for collecting cells. Moreover, the body vessels for which cell collection is desired can vary greatly from patient to patient. To collect the cells, the brush is inserted into the cavity and brushed against the cavity wall repeatedly, with pressure applied to the wall by the brush so that bristles contact the cavity. This brushing can often lead to bleeding, while collecting only a limited number of desired cells from a limited and inconsistent area of the cavity.

SUMMARY

A medical device for collecting cells is provided, the device comprising: a rotatable drive wire having a proximal portion and a distal portion, the proximal portion defining a longitudinal axis; an offset portion defined by the distal portion, wherein the offset portion is spaced radially away from the longitudinal axis such that rotation of the proximal portion of the drive wire causes eccentric rotation of the offset portion relative to the longitudinal axis of the drive wire; and a cell collecting head member mounted to the offset portion of the wire for rotation therewith.

In another form, the distal portion includes a transition portion extending from a point on the longitudinal axis to the offset portion.

In another form, the transition portion is angled between 25-75 degrees relative to the longitudinal axis.

In another form, the cell collecting head member comprises a tube having longitudinal striations extending along an outer surface thereof.

In another form, the cell collecting head member comprises open celled foam.

In another form, the cell collecting head member comprises closed celled foam.

In another form, the cell collecting head member comprises a brush having a plurality of bristles.

In another form, the brush is coupled to the offset portion via crimped cannula.

In another form, the cell collecting head member comprises a coiled wire.

In another form, the cell collecting head member includes a lumen extending longitudinally therethrough, the offset portion extends through the lumen, and the cell collecting head member is rotatably mounted to the offset portion for rotation relative thereto.

In another form, the head is immovably fixed to the offset portion.

In another form, the device further comprises a sheath housing the drive wire, the offset portion, and the cell collecting head member.

In another form, the offset portion is radially compressed within the sheath when housed in the sheath relative to when the offset portion is outside the sheath.

In another embodiment, a system for collecting cells is provided, the system comprising: a handle portion; a rotation mechanism housed within the handle portion, the rotation mechanism comprising an axially translatable rack and a gear portion operably coupled to the rack; a rotatable drive wire having proximal and distal portions, the proximal portion being coupled to the gear portion and being rotatably driven by the rotation mechanism in response to axial translation of the rack; an offset portion of the drive wire disposed at the distal portion thereof; and a cell collecting head portion coupled to the offset portion, the head portion rotating eccentrically relative to the proximal portion of the drive wire in response to rotation of the drive wire.

In another form, the rotation mechanism further comprises: a first bevel gear coupled to the rack; a second bevel gear coupled to the first bevel gear; a shaft coupled to the second bevel gear; a slider coupled to the shaft; and a linkage bar coupled to the slider and the first bevel gear.

In another form, the shaft is coupled to the slider via a yoke, the shaft is rotatable relative to the slider, and the shaft and slider axially translate in unison.

In another form, the shaft is coupled to the second bevel gear via a spline connection, the shaft rotates in unison with the second bevel gear, and the shaft translates axially relative to the second bevel gear.

In another form, the shaft comprises the proximal portion of the drive wire.

In another form, the drive wire proximal portion is coupled to the gear portion and the drive wire distal portion is attached to the proximal portion via a coupler therebetween.

In another form, the offset portion is radially offset from the proximal portion approximately between 1 mm and 10 mm, and the head is approximately 1 cm long and between 3 mm and 7 mm thick.

In another embodiment, a method for collecting cells is provided, the method comprising: delivering to a body cavity an offset portion of a rotatable drive wire, the offset portion having a head member coupled thereto; rotating the drive wire about a longitudinal axis thereof; in response to rotating the drive wire, rotating the offset portion of the drive wire therewith; in response to rotating the offset portion of the drive wire, rotating the head member eccentrically relative to the longitudinal axis of the drive wire; in response to rotating the head member, contacting an inner surface of the body cavity with the head portion to collect cells therefrom.

In another form, the rotation of the drive wire is automatically performed in response to axially translating a rack along the longitudinal axis of the drive wire.

In another form, the method further comprises rotating the head member relative to the offset portion and contacting the inner surface of the body cavity with the entire circumference of the head member.

DETAILED DESCRIPTION

Figure 1:
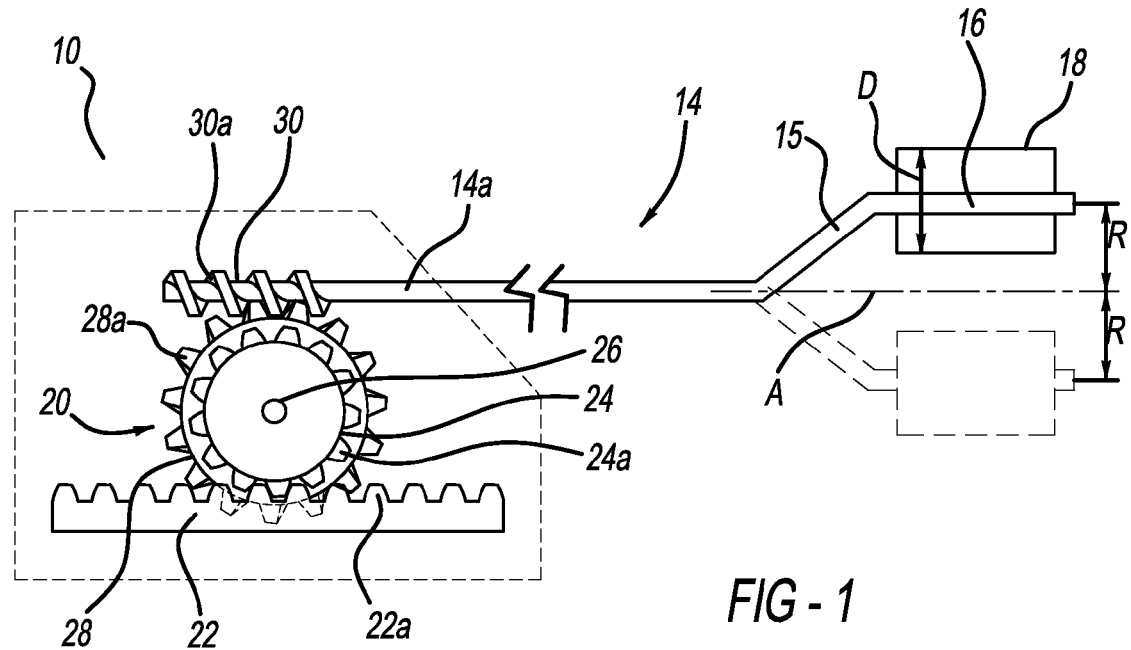
FIG. 1 is a schematic view of a cell collection device having a rotation mechanism, a rotatable drive wire, and a head mounted to an offset portion of the drive wire.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Referring now to the drawings, FIGS. 1-13 illustrate a cell collection device 10 having a handle 12, a drive wire 14 having a proximal portion 14a and a distal portion 14b, where the distal portion 14b includes an angled transition portion 15 and an offset portion 16, and a head 18 attached to the offset portion 16. The head 18 can be used for collected cells from various internal orifices of the body, such as the esophagus, stomach, small and large intestines, biliary duct, pancreatic ducts, urethra, trachea, lungs, and cervix. Of course, cells could also be collected from various other body vessels or cavities.

The handle 12 can include a rotation mechanism 20 for ultimately rotating the distal portion 14b of the drive wire 14. By rotating the distal portion 14b of the drive wire 14, the offset portion 16 will eccentrically rotate relative to the remainder of the drive wire 14, thereby effectively increasing the diameter of the rotation of the head 18. This increase can result in a greater collection area for collecting cells and can result in an increased amount of cells collected relative to a traditional cytology brush. In particular, and with reference to FIG. 9, the entire circumference of a tubular body vessel structure B can be engaged by the head 18 as the head 18 is made to eccentrically rotate with the offset portion 16 about the axis A of the drive wire 14.

The rotation mechanism 20 can be housed within the handle portion 12. In one form, the rotation mechanism 20 includes a rack 22 mounted for axial translation within the housing 12. The rack 22 can include a plurality of teeth 22a extending from the rack 22 in a manner known in the art. The rack 22 can be coupled to a pinion 24. The pinion 24 can be rotatably mounted to the handle 12 via a pin 26, axle, or the like. The pinion 24 can include teeth 24a that couple the pinion 24 to the rack 22, so that axial translation of the rack 22 will cause rotation of the pinion 24 about the pin 26. The pinion 24 can be coupled to a worm wheel 28, so that rotation of the pinion 24 will cause the worm wheel 28 to rotate in unison with the pinion 24. The worm wheel 28 can include teeth 28a extending therefrom. The worm wheel 28 can be coupled to a worm gear 30 that is fixedly coupled to the drive wire 14. The worm gear can include threads 30a that are operably coupled with the teeth 28a of the worm wheel 28, so that rotation of the worm wheel 28 will cause the worm gear 30 and the drive wire 14 coupled thereto to rotate about a common longitudinal axis A of the drive wire 14 and worm wheel 30.

The overall size of the rotation mechanism 20 can vary depending on the needs of the user and the overall desired size of the device 10 and the handle 12. The relative sizes of the various components of the rotation mechanism 20 can also vary depending on desired gear ratios, as is known in the art.

Given the structure of the rotation mechanism 20 described above, the user of the device 10 can cause the drive wire 14 to rotate by translating the rack 22 axially in a direction generally parallel to the axis A of the drive wire 14. For example, by translating the rack 22 toward the distal end of the device 10 (to the right in FIG. 1), the pinion 24 and worm wheel 28 will rotate in a first rotational direction. The rotation of the worm wheel 28 will cause the worm gear 30 to rotate in a first rotational direction that is generally perpendicular to the first rotational direction of the worm wheel 28. The rotation of the worm gear 30 causes the drive wire 14 to rotate in the same direction.

Similarly, by translating the rack 22 in the opposite direction, the pinion 24 and worm wheel 28 will rotate in a second rotational direction that is opposite the first rotational direction. The worm gear and drive wire 14 will likewise rotate in a second rotational direction opposite the first rotational direction.

Thus, by reciprocating the rack 22 axially, the drive wire 14 can be made to rotate back and forth. Alternatively, by translating the rack 22 in single direction a relatively long distance, the drive wire 14 can be rotated multiple times in the same rotational direction. Of course, it will be appreciated that a user could tailor the amount of the rotation and/or reciprocal rotation of the drive wire 14 by altering the stroke of the rack 22 as desired.

The drive wire 14 can be constructed so that it remains torsionally strong while retaining flexibility for being pushed through a tortuous body vessel. Additionally, the drive wire 14 can be constructed to retain pushability for being fed into the body vessel without collapsing. In one form, the drive wire 14 can be made from stainless steel, Nitinol, a filament cable having multiple twisted layers, multiple wound wires or single wires which may be solid or tubular in form, as well as combinations thereof. Each of the above constructions can be sized to allow for pushability, torqueability, and flexibility without undue experimentation. In one form, the drive wire 14 can be approximately 1 mm in diameter, but could be smaller, such as in the range of 0.3 mm to 1 mm; however, other sizes or size ranges could also be used depending on the needs and desires of the user. At least one example of drive wire construction can be found in U.S. Pat. No. 5,243,996, filed Jan. 3, 1992, which is hereby incorporated by reference in its entirety.

The drive wire 14, as described above, includes the offset portion 16 at the distal end. The offset portion 16 can be integral with the remainder of the drive wire 14, having approximately the same thickness and constructed as the remainder of the drive wire 14. The offset portion 16 is generally parallel to the axis A of the drive wire 14, so that rotation of the drive wire about its axis will cause the offset portion 16 to rotate about the axis. The offset portion 16 can be offset a radial distance R. Thus, the diameter of the rotation of the offset portion 16 is approximately 2R. When combined with a head 18 having a general thickness of diameter D, the effective diameter of the rotating device 10 that will contact the circumference of a tubular body is about 2R+D, as shown in FIG. 1. The tubular body structure from which cells are to be collected preferably has a diameter less than or equal to 2R+D, but can be greater. The amount of offset R can vary depending on the needs of the user, or the size of the contemplated body vessel. In one form, the offset can be approximately 3-5 mm to be used, for example, in the biliary system. However, other offsets could also be used, such as 2-5 mm for use in a blood vessel. In the esophagus, the offset could be approximately 7-15 mm. In the colon, the offset could be as large as approximately 1-2 cm. Because the effective diameter of the rotating device depends also on the general thickness or diameter D of the head 18, the offsets can be adjusted to account for varying thicknesses of the head 18 to match the general diameter of the contemplated body cavity.

The device 10 can further include the head 18 mounted to the offset portion 16 of the drive wire 14. The head 18 can be mounted for rotation relative to the offset portion 16, or the head can fixedly mounted to the offset portion 16, depending on the style of the head 18, further described below. The head 18 can be in the form of one of many appropriate cell collection materials. Some examples of cell collection devices can be found in U.S. Pat. No. 5,713,369, filed Sep. 13, 1995, U.S. Pat. No. 6,346,086, filed Apr. 23, 1999, and U.S. Pat. No. 8,070,691, filed Dec. 9, 2008, each of which are hereby incorporated by reference in their entirety. By being mounted to the offset portion 16 of the drive wire 14, the head 18 can be allowed to pass across the surface of the body vessel as the drive wire 14 rotates.

Figure 2:
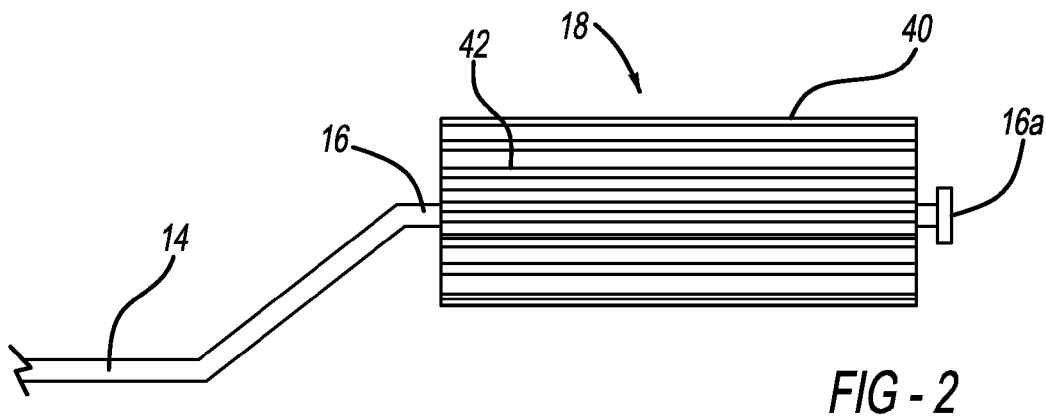
FIG. 2 is a front view of a first embodiment of the head.
Figure 3:
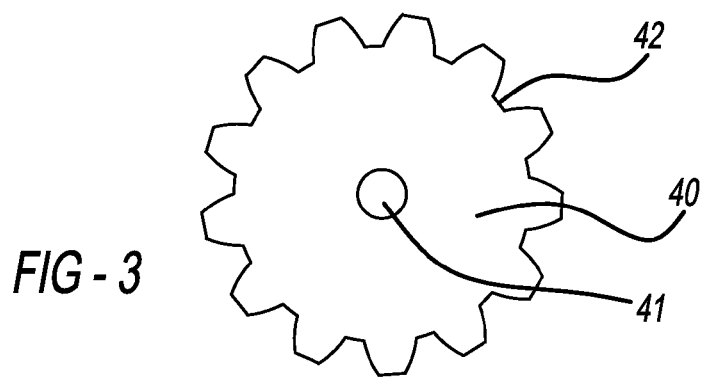
FIG. 3 is a side view of the first embodiment of the head.

In one form, as shown in FIGS. 2 and 3, the head 18 can be in the form of a generally cylindrical tube 40. The tube 40 can be generally rigid, if desired. The tube 40 can be approximately 1 cm in length and approximately 2-3 mm thick in diameter. Of course, other lengths and thicknesses could also be used. The tube 40 can be made from polyethylene, PTFE, PEBAX, polyurethane, silicone, or another material known in the art suitable for cell collection.

In this form, the tube 40 can include a lumen 41 extending through the center of the tube 40. The tube 40 can be mounted for rotation relative to the distal portion 16 by inserting the distal portion 16 through the lumen 41, shown in FIG. 3. As the offset portion 16 is made to eccentrically rotate, the tube 40 can roll across the surface of the body cavity to collect cells about the entire circumference of the tube 40. Of course, it will be appreciated that the tube 40 could also be fixedly mounted to the offset portion 16 so that it does not rotate relative to the offset portion 16.

The tube 40 can include a plurality of longitudinal striations 42 or ridges extending along the tube 40. These striations 42 can be used to collect and store cells from the body vessel as the head 18 is rotating and contacting the surface of the body vessel.

In another form, the head 18 can be in the form of an open celled foam 50 or closed cell foam 52. In the case of the foam 50 or 52, they can be sized similar to the tube 40, with a length of approximately 1 cm and a thickness of approximately 2-3 mm. The open celled foam 50 can be made from polyurethane or another biocompatible material. The closed cell foam 52 can be made from polyethylene of another biocompatible material. In either case, the foam 50 or 52 can rotate relative to the distal portion 16 of the drive wire 14 and roll along the body vessel, similar to the tube 40, or it can be fixedly mounted. The rotation and rolling of the foam 50 or 52 can allow the foam 50 or 52 to come into contact with the body vessel about the entire circumference of the foam 50 or 52. The open or closed cell arrangement of the foam 50 or 52 allows it to sufficiently collect and store cells from the contact with the body vessel.

Figure 4:
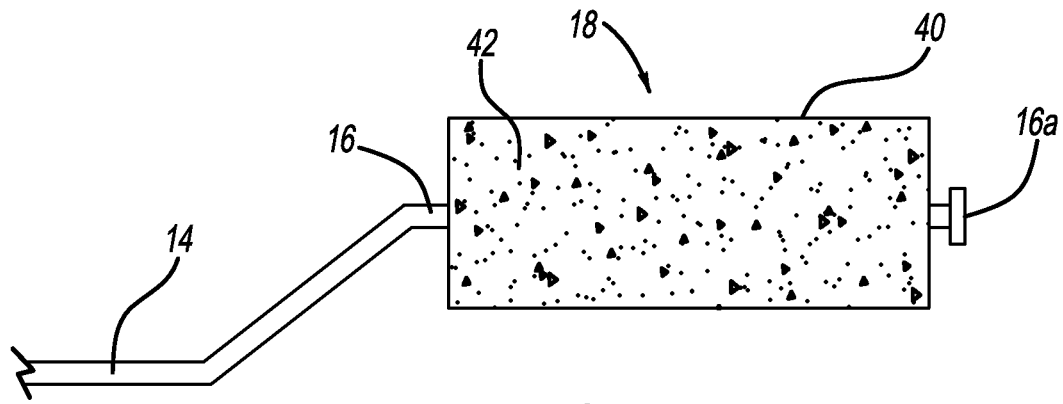
FIG. 4 is a front view of a second embodiment of the head.

In one form, as shown in FIG. 4, the foam 50 or 52 can be mounted to an inner core portion 54 that is mounted for rotation to the offset portion 16. In this form, the core 54 is free to rotate relative to the offset portion 16, and the foam 50 or 52, being fixedly mounted to the core 54, will rotate along with the core 54. The core 54 can include a lumen (not shown) similar to the lumen 41 of the tube 40 to allow the foam 50 or 52 to rotate relative to the offset portion 16.

The tube 40 and foams 50 and 52 can be mounted to the offset portion 16 and held in place by a stop portion 16a of the offset portion 16. The stop portion 16a is sized larger than the outer diameter of the offset portion 16 and the inner diameter of the tube 40 or foams 50 and 52, thereby preventing the tube 40 or foams 50 or 52 from sliding off the end of the offset portion 16.

Figure 5:
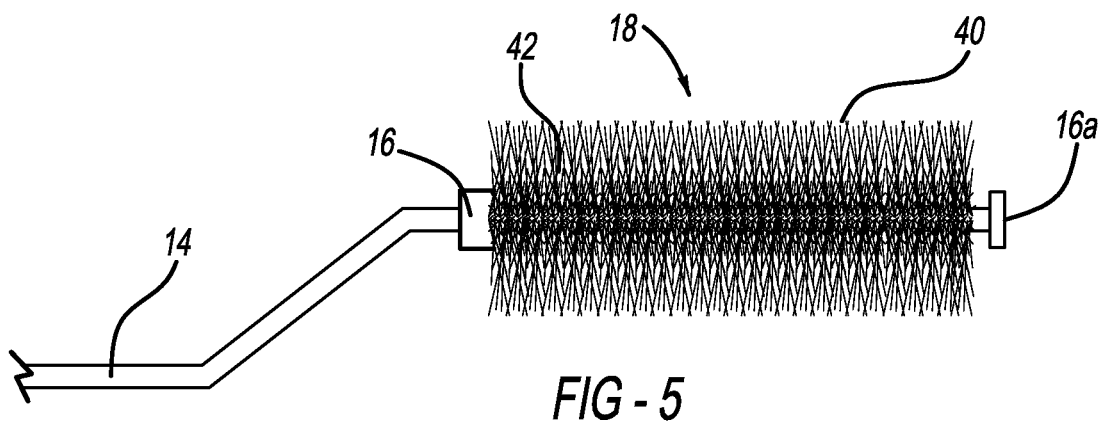
FIG. 5 is a front view of a third embodiment of the head.

In another form, as shown in FIG. 5, the head 18 can be in the form of a brush 60. The brush 60 can include a plurality of bristles 62 extending radially outward. The bristles 62 can be made from nylon or another biocompatible material. The bristles 62, if desired, could be made from the same material as a traditional cytology brush having plastic bristles. The offset rotation of the brush 60, rather than the traditional scraping or brushing, will reduce trauma relative to the traditional cytology brush.

The brush 60 can be coupled to the offset portion via a coupling cannula 64. The cannula 64 can be crimped at one end to the offset portion of the drive wire 14, and the opposite end to the brush 60. The brush 60 can include an atraumatic tip 66 having a generally rounded shape at the distal end. The atraumatic tip 66 can reduce trauma to the patient in the event the distal end comes into contact with the wall of the body vessel. Similar to the other sizes described above, the brush can be generally 1 cm in length and 3-7 mm thick; however, other sizes could also be used.

Figure 6:
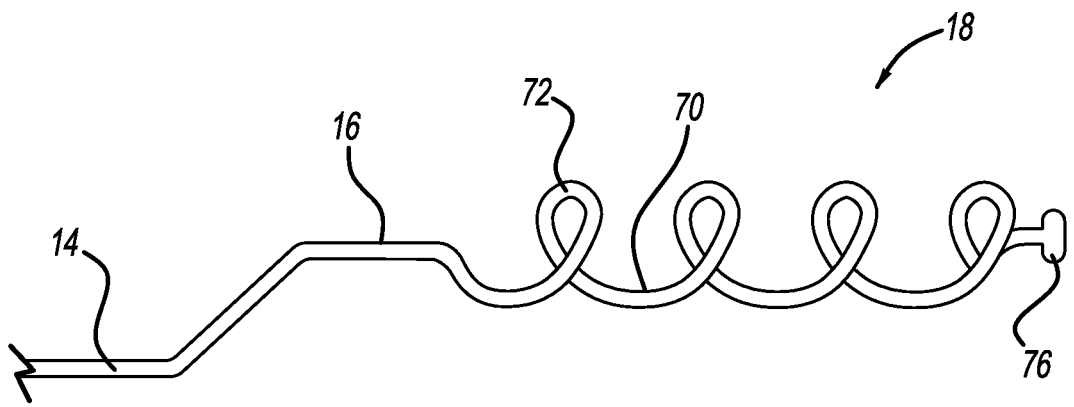
FIG. 6 is a front view of a fourth embodiment of the head.
Figure 7:
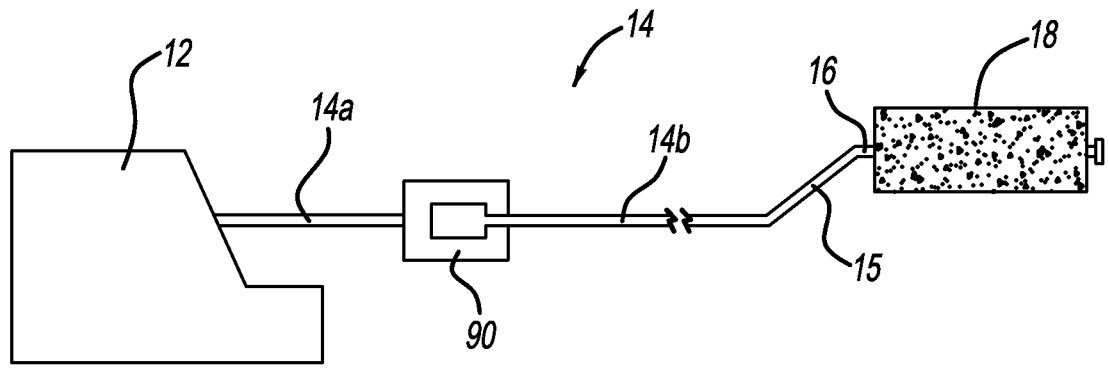
FIG. 7 is a schematic view of a two-piece drive wire.

In another form, as shown in FIG. 6, the head 18 can be in the form of a coiled wire 70. The coiled wire 70 can be integrally formed as one piece with the offset portion 16 and the remainder of the drive wire 14. The coiled wire 70 can be made from Nitinol and be approximately 1 cm in the length and 2-3 mm in diameter of the coiled shape. The coiled wire 70 can include plurality of spaced apart coils 72 such that it is in the form of an open coil, where the area between the coils 72 is generally free from other material. Thus, cells can be collected and stored in this open area. The coiled wire 70 can include an atraumatic tip 76 having a general rounded shape at the distal end to limit trauma to the patient in the event the tip contacts the body vessel.

The drive wire 14 has been described above as being one piece extending from the handle to the offset portion 16, such that rotation of the worm gear 30 causes the drive wire 14 connected thereto to rotate about its axis. However, the drive wire 14 can have a two piece construction, shown in FIG. 7, so that the distal portion 14b of the drive wire 14, including the offset portion 16 and head 18 can be disposed of after use, and the handle 12 and rotation mechanism 20 can be re-used with a new distal offset portion 16 and head 18. In this form, the drive wire 14 can include a coupler 90 for coupling a distinct proximal portion 14a with a distinct distal portion 14b. The distal portion 14*b* includes the offset portion 16, which can be disposed of after use while retaining the proximal portion 14*a* along with the handle 12 and rotation mechanism 20. This two piece construction can be used with the various embodiments described herein.

Figure 8:
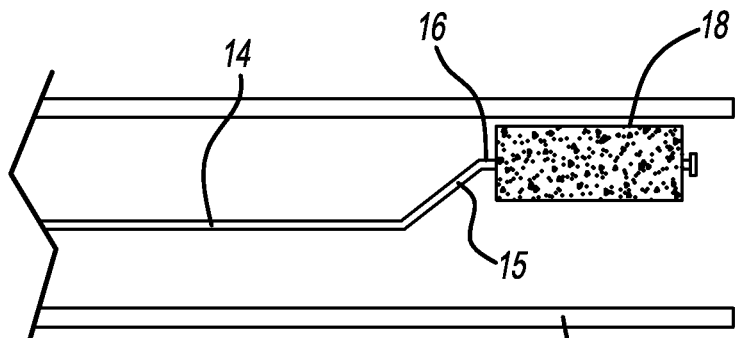
FIG. 8 is a cross-sectional schematic view of the drive wire and head disposed within a delivery sheath.
Figure 9:
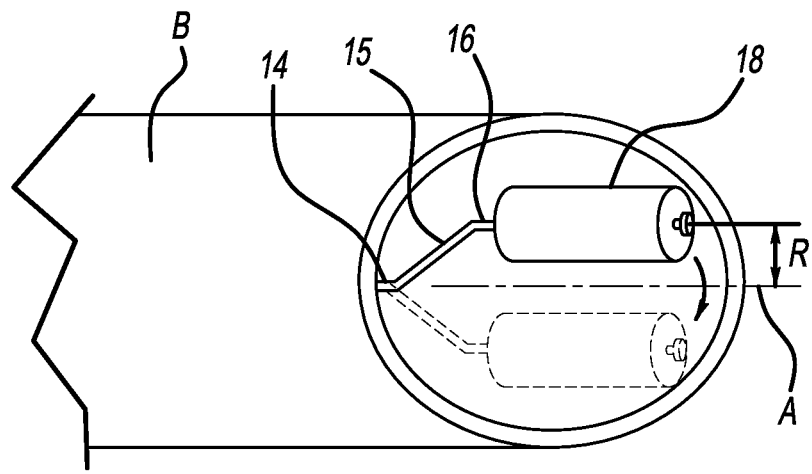
FIG. 9 is an isometric view of the drive wire and head disposed within a tubular body vessel, showing the rotation of the head about the body vessel.

With reference to FIG. 8, in one form, the drive wire 14, the offset portion 16, and the head 18 can be housed within a sheath 92 for delivery to the desired body vessel. The sheath 92 allows the head 18 to be covered such that the head 18 can be generally limited from collecting cells until being deployed at the desired body cavity. The sheath 92 can also reduce trauma to the patient by limiting the contact between the head 18 and the body vessel in which the sheath 92 is disposed. When housed within the sheath 92, the offset portion 16 can be compressed such that the offset distance is smaller than when the offset portion 16 is outside the sheath 92. In this position, also known as a delivery configuration, the angled transition portion 15 can flex to allow the offset portion 16 to move inward relative to its exposed and expanded configuration. The drive wire 14 could thereby be generally straight in the delivery configuration. The drive wire 14 can have shape memory characteristics to cause the offset portion 16 to spring outward to the desired offset when the offset portion 16 becomes disposed outside the sheath 92.

The flexibility of the angled transition portion 15, as well as other portions of the drive wire 14, can allow for a similar effect when the device 10 is disposed within a body vessel B having a diameter that is less than the overall effective diameter of the device 10. The head 18 and offset portion 16 can flex inward in such a situation, and the rotation of the head 18 can occur within the reduced diameter body vessel while contacting the entire circumference of the body vessel when rotated. This inward flexibility of the head 18 can enable increased cell collection while limiting trauma to the patient. An example of the head 18 within the body vessel B can be seen in FIG. 9.

As described above, the rotation mechanism 20 can convert linear motion of the rack 22 into rotational motion of the drive wire 14 and the offset portion 16 connected thereto. With reference to FIGS. 9-12, in an alternative embodiment, a rotation mechanism 120 can convert linear motion of a rack 122 in a single direction into rotational motion of the drive wire 14 in a single rotational direction as well as reciprocating translation of the drive wire 14. Thus, the rotation mechanism 120 can cause the offset portion to move axially without requiring the user to manually reciprocate the handle 12.

The rotation mechanism 120 can be incorporated into the handle 12 and actuated in a manner known in the art. For example, the mechanism 120 can be housed within a pistol-style grip, or a lever meant to be squeezed with several fingers, or a three-ring type handle. Of course, other handle configurations could also be used. The mechanism 120 can operate to rotate and reciprocate the drive wire 14 regardless of the particular direction that the rack 122 translates.

Figure 10:
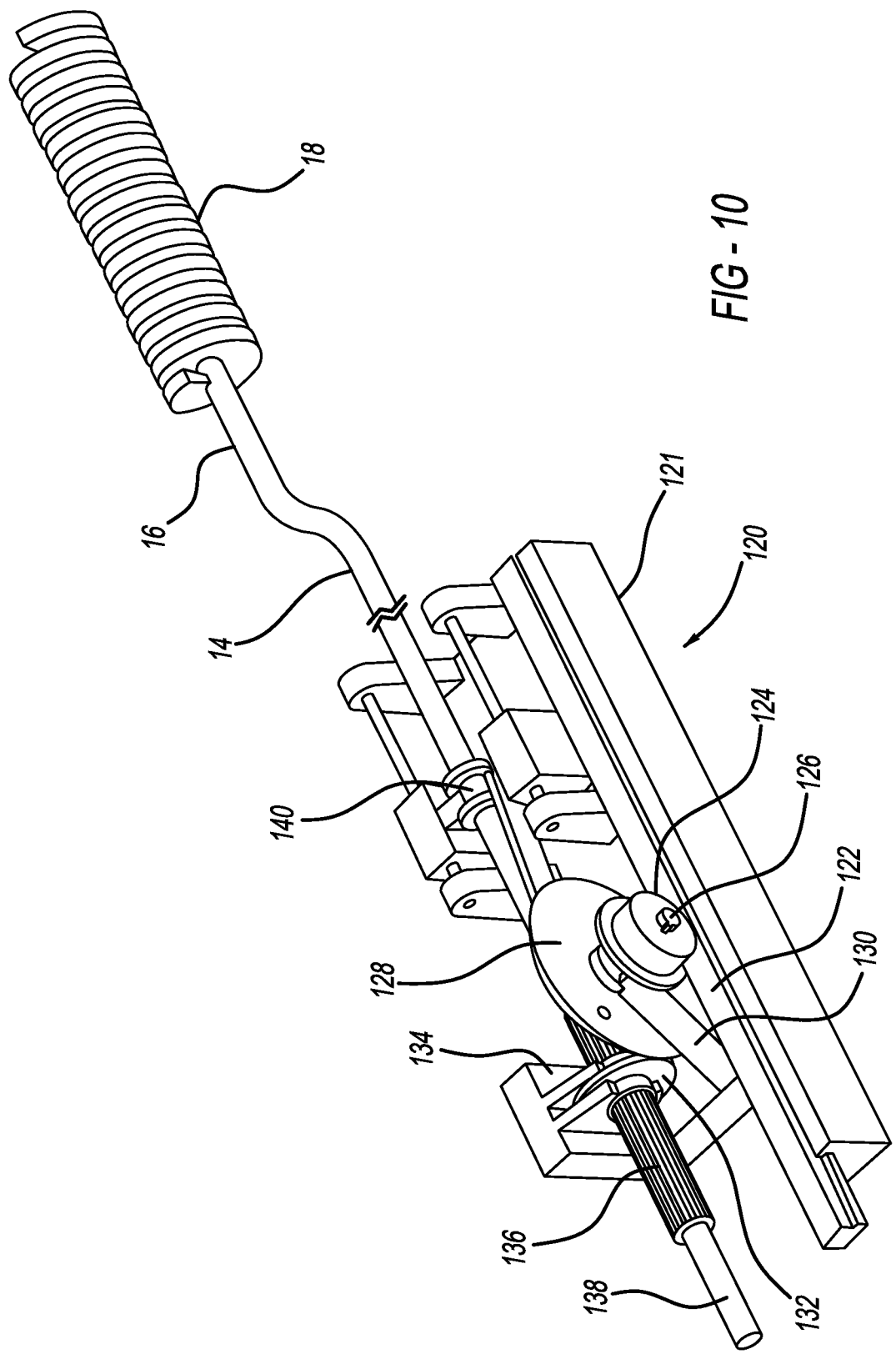
FIG. 10 is of a second embodiment of the rotation mechanism having a rack, a pinion, a first bevel gear, and a second bevel gear for rotating a shaft.

With reference to FIG. 10, the rotation mechanism 120 can include a base 121 to which the various components of the mechanism 120 are mounted. The rack 122 is mounted for axial translation or sliding along the major axis of the base 121. The rack 122 can axially translate in either direction. The rack 122 can be coupled to a pinion 124 that is fixedly mounted to a gear shaft 126. A bevel gear 128 is likewise fixedly mounted to the gear shaft 126. The gear shaft 126 is mounted for rotation to a bearing portion 130 of the base. Thus, rotation of the pinion 124 will cause the gear shaft 126 to rotate, thereby rotating the bevel gear 128.

The bevel gear 128 is rotationally coupled to a second bevel gear 132 that is orientated generally perpendicular to the bevel gear 128. The second bevel gear 132 is constrained by a second bearing portion 134 of the base 121, allowing the second bevel gear 132 to rotate but restricting from moving axially. The rotational axis of the second bevel gear 132 is generally aligned perpendicular to the major axis of the base 121.

Figure 11:
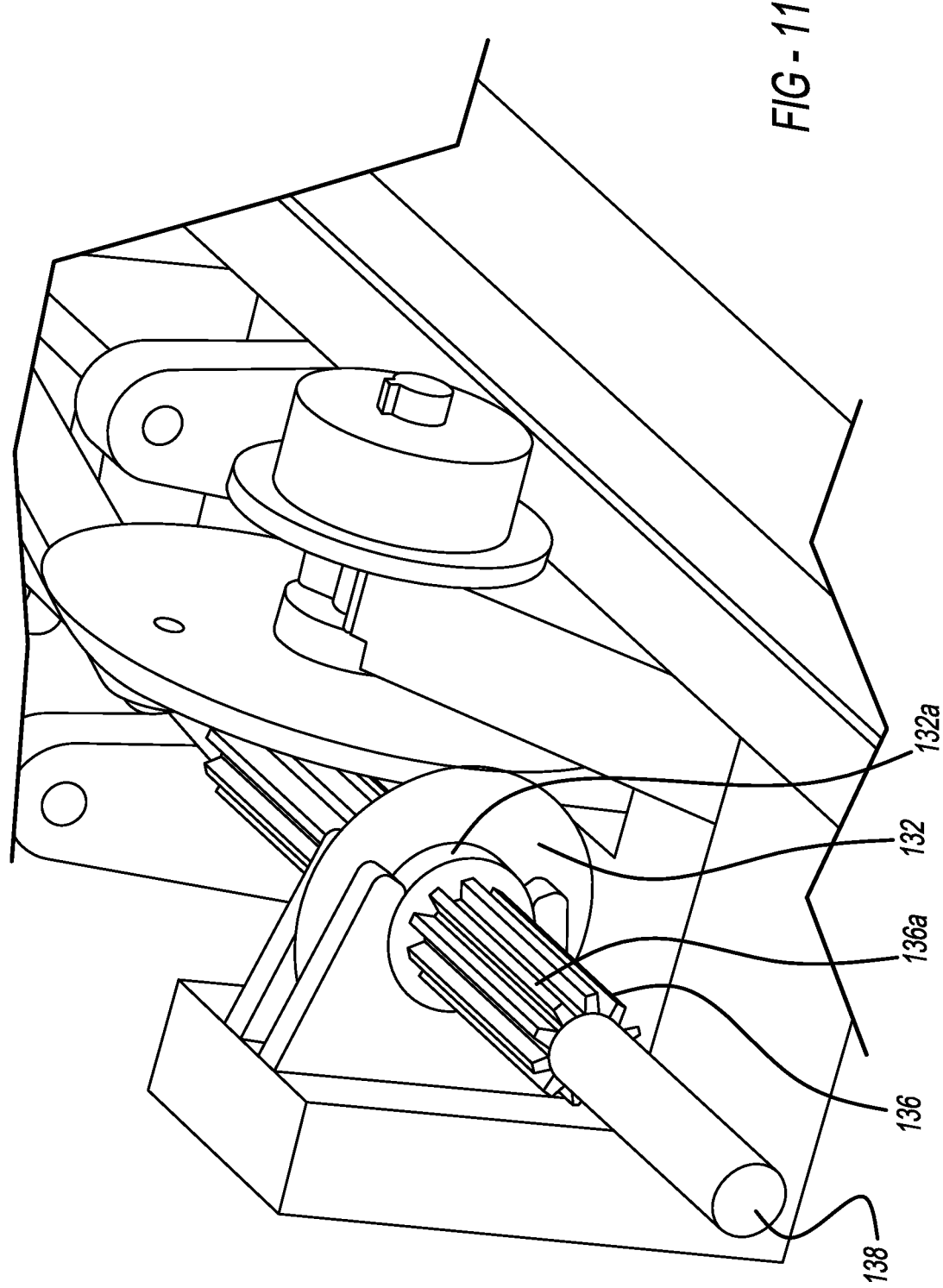
FIG. 11 is an isometric view of the second embodiment of the rotation mechanism illustrating the second bevel gear, a spline, and a shaft.

With reference to FIG. 11, the second bevel gear 132 can be slidably coupled to a spline 136. The spline 136 can include teeth 136*a* that correspond to the shape of an internal bore 132*a* of the second bevel gear 132. Thus, rotation of the second bevel gear 132 will cause the spline 136 to rotate therewith, while permitting the spline 136 to translate axially relative to the second bevel gear 132.

The spline 136 can be attached, or integrally formed, with a shaft 138. The shaft 138 extends longitudinally parallel to the major axis of the base 121. Due to the attachment to the spline 136, rotation of the spline 136 will thereby cause the shaft 138 to rotate therewith.

Figure 12:
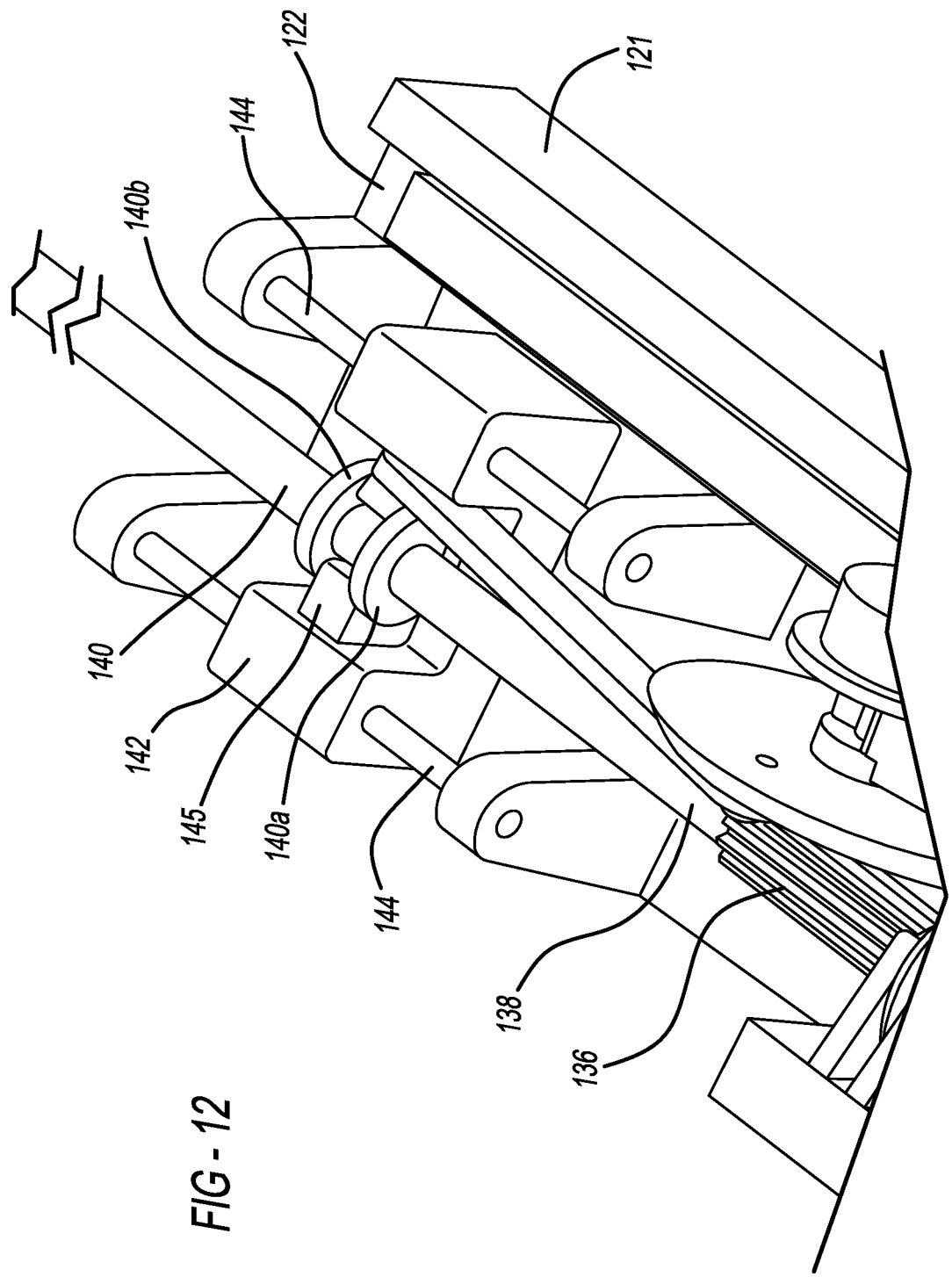
FIG. 12 is an isometric view of the second embodiment of the rotation mechanism illustrating a yoke and a slider.

With reference to FIG. 12, the shaft 138 can also include a yoke 140 disposed distally from the second bevel gear 132. The yoke 140 includes a first flange 140*a* and a second flange 140*b*. The yoke 140 can be integrally formed with the shaft 138, or otherwise secured so as to move in unison with the shaft 138.

The mechanism 120 further includes a slider 142 that is mounted to a pair of longitudinally extending rods 144 to allow the slider 142 to translate axially. The slider 142 includes a bearing portion 145 that is coupled to the shaft 138 within the yoke 142. The slider 142 thereby supports the shaft 138 at the yoke and allows the shaft 138 to rotate relative to the slider 142. With the slider 142 coupled to the shaft 138 within the yoke 140, the slider 142 will translate axially in unison with the shaft 138. The translation can occur while the shaft 138 is rotating.

Figure 13:
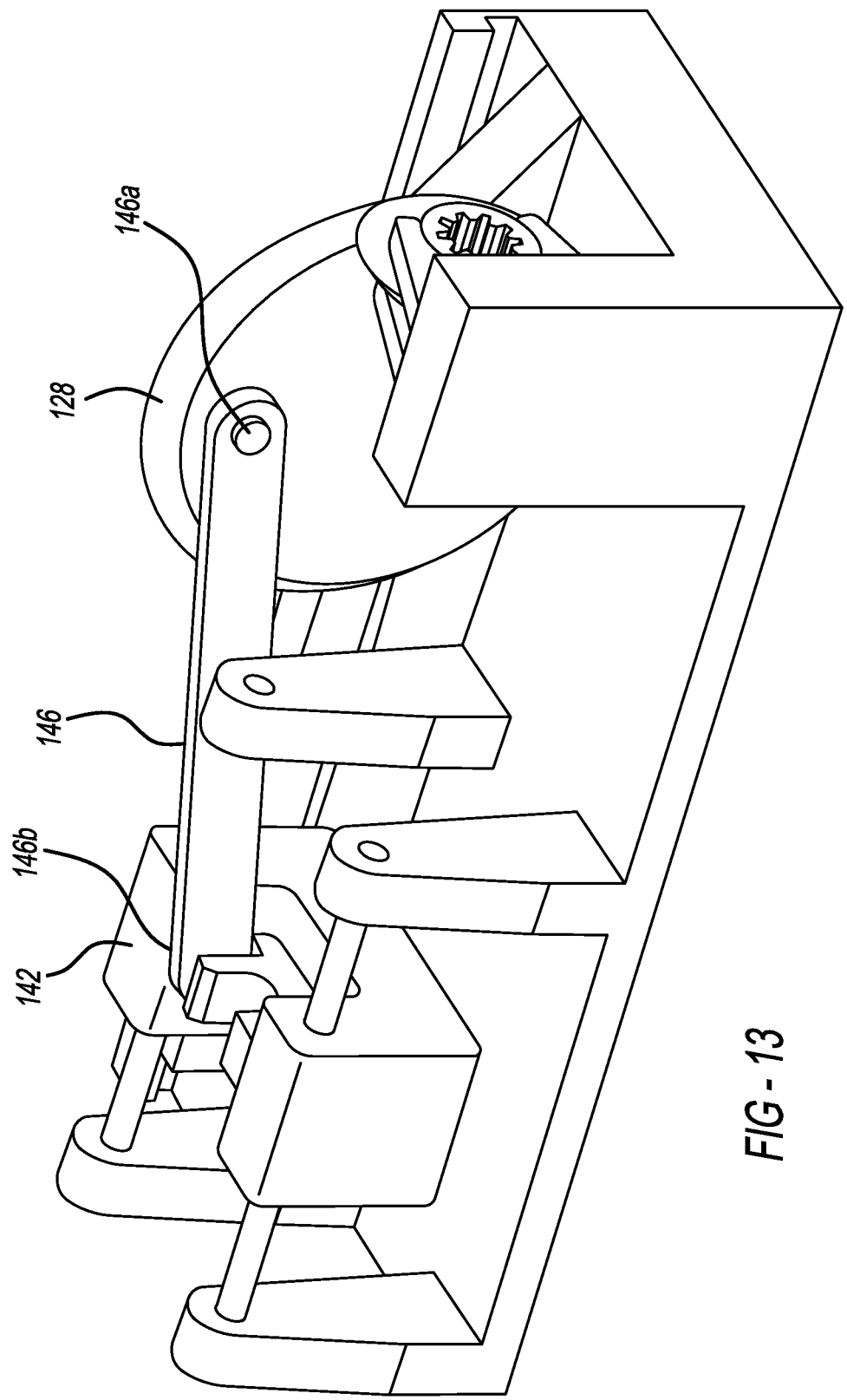
FIG. 13 is an isometric view of the second embodiment of the rotation mechanism illustrating a linkage bar between the slider and the first bevel gear.

With reference to FIG. 13, the slider 142 is further coupled to the bevel gear 128 via a link member 146. The link member 146 can be in the form of an elongate bar. The link member 146 is coupled to both the bevel gear 128 and the slider 142 via pivot pins 146*a* and 146*b*, respectively. The link member 146 is coupled to the bevel gear 128 radially away from the rotational axis of the bevel gear 128. Thus, rotation of the bevel gear 128 will cause the link member 146 to move in a circular pattern. By being coupled to the bevel gear 128 and slider 146 via the pivot pins 146*a*, 146*b*, rotation of the bevel gear 128 will cause the slider 142 to reciprocally translate in response to rotation of the bevel gear 128 in a single direction.

As described above, the slider 142 translates in unison with the shaft 138 due to the connection at the yoke 140. Thus, as the slider 146 reciprocates, the shaft 138 will reciprocate in unison while simultaneously being rotated in a single rotational direction by the second bevel gear 132.

The shaft 138 can extend from the handle 12 and be coupled to the drive wire 14, so that the rotational and reciprocal axial movement of the shaft 138 can be transferred to the drive wire 14, and the offset portion 16 and the various embodiments of the head 18 described above. The shaft 138 and drive wire 14 can be coupled via the coupler 90, previously described, thereby allowing the drive wire 14 and head 18 to be disposed of after use. Alternatively, if re-use of the handle 12 and mechanism 120 is not desired, necessary, or possible, the shaft 138 can be integrally formed with the drive wire 14.

Having described the general structure of the various embodiments of the device 10 above, the use of the device 10 will now be described.

The device 10 can be inserted into the body toward the desired body cavity in a manner known in the art, such as directly into a body orifice or through the patient's skin percutaneously. The drive wire 14, possibly housed within the sheath 92, can be pushed and delivered to the desired body cavity. Once at the desired location for collecting cells, the sheath 92 can be refracted proximally to expose the head 18 and the offset portion 16, or the drive wire 14 moved distally to expose the head 18.

With the head 18 positioned within the desired body cavity, the rack 22 or 122 can be translated axially in a first direction. The translation of the rack 22 or 122 will cause the drive wire 14 to rotate, causing the offset portion 16 to rotate eccentrically. The head 18 will rotate with the offset portion 16 to collect cells from the body cavity. In some forms, the head 18 can rotate relative to the offset so that the head 18 will roll along the body cavity and the circumference of the head 18 will contact the body cavity to collect cells.

In the case of the rotation mechanism 120, translation of the rack 122 will also cause the drive wire 14, and the offset portion 16 and head 18 coupled thereto, to reciprocate axially in addition to the rotation of the drive wire 14. This reciprocal translation can increase the area of the body cavity that is contacted by the head 18, thereby increasing the amount of cells that can be collected. In the case of the rotation mechanism 20, the device 10 can be manually reciprocated to increase the area of the body cavity from which cells are collected.

The rack 22 or 122 can be further translated in a direction opposite to the initial axial translation. This opposite axial translation will cause the offset portion 16 and head 18 to rotate in the opposite direction, allowing for additional cell collection.

After the rotation of the offset portion 16 and head 18 is complete, and the cells have been collected on the head 18, the sheath 92 can be advanced back over the head 18 or the head 18 can be retracted into the sheath 92. The head 18 having the cells can then be retracted back out of the body via the path of insertion. The collected cells can thereby be retrieved and examined in a manner known in the art.

The above description of use can apply to each of the embodiments of the head 18 described above. In the case of the tube 40 or foams 50 and 52, the head 18 will generally rotate about the offset portion 16 when in contact with the body cavity. In the case of the brush 60 or coiled wire 70, the head 18 will generally not rotate relative to the offset portion 16, because the brush 60 and coiled wire 70 are generally not mounted for rotation to the offset portion 16. However, it will be appreciated that the brush 60 and coiled wire 70 could be mounted for rotation to the offset portion 16 if desired, thereby allowing for rotation relative thereto.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A medical device for collecting cells from a bodily structure, the device comprising:
    a rotatable drive wire having a proximal portion and a distal portion, the proximal portion defining a longitudinal axis;
    an offset portion defined by the distal portion, wherein the offset portion is spaced radially away from the longitudinal axis such that rotation of the proximal portion of the drive wire causes eccentric rotation of the offset portion relative to the longitudinal axis of the drive wire; and
    a cell collecting head member mounted to the offset portion of the wire for rotation therewith;
    wherein the cell collecting head member defines a generally cylindrical outer profile and includes an outer surface sized and positioned to engage the bodily structure and collect cells.

2. The device of claim 1, wherein the distal portion includes a transition portion extending from a point on the longitudinal axis to the offset portion.

3. The device of claim 2, wherein the transition portion is angled between 25-75 degrees relative to the longitudinal axis.

4. The device of claim 1, wherein the cell collecting head member comprises a tube having longitudinal striations extending along an outer surface thereof.

5. The device of claim 1, wherein the cell collecting head member comprises open celled foam.

6. The device of claim 1, wherein the cell collecting head member comprises closed celled foam.

7. The device of claim 1, wherein the cell collecting head member comprises a brush having a plurality of bristles.

8. The device of claim 7, wherein the brush is coupled to the offset portion via crimped cannula.

9. The device of claim 1, wherein the cell collecting head member is rotatably mounted to the offset portion for rotation relative thereto, wherein the cell collecting head member rotates relative to the offset portion in response to contacting bodily tissue when the drive wire is rotated.

10. The device of claim 1, wherein the head is immovably fixed to the offset portion.

11. The device of claim 1, further comprising a sheath housing the drive wire, the offset portion, and the cell collecting head member.

12. The device of claim 11, wherein the offset portion is radially compressed within the sheath when housed in the sheath relative to when the offset portion is outside the sheath.

13. The device of claim 1 further comprising:
    a handle portion;
    a rotation mechanism housed within the handle portion, the rotation mechanism comprising an axially translatable rack and a gear portion operably coupled to the rack;
    the proximal portion of the rotatable drive wire being coupled to the gear portion and being rotatably driven by the rotation mechanism in response to axial translation of the rack;
    the head member rotating eccentrically relative to the proximal portion of the drive wire in response to rotation of the drive wire.

14. The device of claim 13, wherein the rotation mechanism further comprises:
    a first bevel gear coupled to the rack, the first bevel gear rotating in response to axial translation of the rack;
    a second bevel gear coupled to the first bevel gear, the second bevel gear rotating in response to rotation of the first bevel gear;
    a shaft coupled to the second bevel gear, the shaft rotating in unison with the second bevel gear;
    a slider coupled to the shaft and being longitudinally fixed relative to the shaft while allowing the shaft to rotate relative to the slider; and
    a linkage bar coupled to the slider and the first bevel gear, the linkage bar being connected to the first bevel gear at a location radially offset from an axis of rotation of the first bevel gear;

wherein axial translation of the rack causes rotation of the shaft via the first and second bevel gears and simultaneously causes axial movement of the shaft via the linkage bar that connects the first bevel gear and the slider.

15. The device of claim 14, wherein the shaft is coupled to the slider via a yoke, and the shaft and slider axially translate in unison.

16. The device of claim 14, wherein the shaft is coupled to the second bevel gear via a spline connection, and the shaft translates axially relative to the second bevel gear.

17. The device of claim 14, wherein the shaft comprises the proximal portion of the drive wire.

18. The device of claim 13, wherein the drive wire proximal portion is coupled to the gear portion and the drive wire distal portion is attached to the proximal portion via a coupler therebetween.

19. The device of claim 13, wherein the offset portion is radially offset from the proximal portion approximately between 1 mm and 10 mm, and the head is approximately 1 cm long and between 3 mm and 7 mm thick.

20. A method for collecting cells from a bodily structure, the method comprising:
 delivering to a bodily structure an offset portion of a rotatable drive wire, the offset portion having a head member coupled thereto, wherein the head member defines a generally cylindrical outer profile with an outer surface sized and configured to engage the bodily structure and collect cells;
 rotating the drive wire about a longitudinal axis thereof;
 in response to rotating the drive wire, rotating the offset portion of the drive wire therewith;
 in response to rotating the offset portion of the drive wire, rotating the head member eccentrically relative to the longitudinal axis of the drive wire;
 in response to rotating the head member, contacting an inner surface of the body cavity with the head portion to collect cells therefrom.

21. The method of claim 20, wherein the rotation of the drive wire is automatically performed in response to axially translating a rack along the longitudinal axis of the drive wire.

22. The method of claim 20 further comprising rotating the head member relative to the offset portion and contacting the inner surface of the body cavity with the entire circumference of the head member.

23. The device of claim 1, wherein the outer surface of the cell collecting head member is sized and structured to collect cells when the drive wire is rotated in either rotational direction.

24. The method of claim 20 further comprising rotating the drive wire in a first rotational direction and collecting cells during the rotation in the first rotational direction, and rotating the drive wire in a second rotational direction that is opposite the first rotational direction and collecting cells during the rotation in the second rotational direction.

* * * * *